United States Patent
Makuuchi et al.

(10) Patent No.: US 8,035,071 B2
(45) Date of Patent: Oct. 11, 2011

(54) CONTAMINATION-INSPECTING APPARATUS AND DETECTION CIRCUIT

(75) Inventors: Masami Makuuchi, Yokohama (JP); Ritsurou Orihashi, Tokyo (JP); Masayoshi Takahashi, Yokohama (JP); Wen Li, Yokohama (JP); Kengo Imagawa, Fujisawa (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 682 days.

(21) Appl. No.: 12/116,241

(22) Filed: May 7, 2008

(65) Prior Publication Data

US 2008/0278717 A1    Nov. 13, 2008

(30) Foreign Application Priority Data

May 9, 2007   (JP) ................. 2007-124082

(51) Int. Cl.
*G01N 21/88* (2006.01)
(52) U.S. Cl. ............... 250/214 A; 250/214 AG
(58) Field of Classification Search .... 356/237.2–237.5; 250/214 AG, 214 A, 214 AC
See application file for complete search history.

(56) References Cited

U.S. PATENT DOCUMENTS 6,744,261 B2    6/2004  Yamanaka
6,833,913 B1 *  12/2004 Wolf et al. ................. 356/237.2

FOREIGN PATENT DOCUMENTS

| JP | 01-160537 | 6/1989 |
| JP | 07-241287 | 9/1995 |
| JP | 08-145899 | 6/1996 |
| JP | 08-320294 | 12/1996 |
| JP | 2000-088535 | 3/2000 |
| JP | 2002-271202 | 9/2002 |
| JP | 2002-300036 | 10/2002 |
| JP | 2005-526239 | 9/2005 |

* cited by examiner

*Primary Examiner* — Tony Ko
(74) *Attorney, Agent, or Firm* — Antonelli, Terry, Stout & Kraus, LLP.

(57) ABSTRACT

The detection part has: a subtraction module for calculating correction data from data of detection systems when a reference-voltage generation module applies a reference voltage to the detection systems; a data-holding module for holding the correction data; an addition module for making a correction of detection data; a comparison module for comparing the detection data with switching data; and a selector for switching data of the detection systems including data subjected to the correction according to the output of the comparison module.

9 Claims, 5 Drawing Sheets

(1) Output Code after Logarithmic Conversion

FIG.2B

(2) Output Code after Switching by Selector

CONTAMINATION-INSPECTING APPARATUS AND DETECTION CIRCUIT

CLAIM OF PRIORITY

The present application claims priority from Japanese application serial no. JP 2007-124082, filed on May 9, 2007, the content of which is hereby incorporated by reference into this application.

BACKGROUND OF THE INVENTION

1. Field of the Invention

The present invention relates to a contamination-inspecting apparatus for inspecting a semiconductor wafer, and specifically it relates to a technique for detecting a signal.

2. Description of the Related Art

A contamination-inspecting apparatus for inspecting a surface of a semiconductor wafer for a contaminant has: an irradiation optical system for irradiating a wafer surface with laser light; a detection optical system for detecting light scattered from the wafer surface; a detection unit for converting the scattered light detected with the detection optical system into electric signals to make a correction; and a display unit for making a judgment on a contaminant to display the result. In the detection unit, a detection circuit is incorporated; usually a signal is output through the detection circuit to make a judgment on a contaminant. Now, with reference to FIG. 5, a detection circuit of a semiconductor wafer contamination-inspecting apparatus, which was considered as a related art by the inventor, will be described in outline. The conventional contamination-inspecting apparatus irradiates a wafer with laser light while rotating the wafer, and detects light scattered and reflected by a contaminant on a wafer and the like by use of PMT (Photo Multiplier Tube) 1. Specifically, the PMT 1 is a device which multiplies incident light by the effect of multiplication of photoelectrons, and then outputs an electric current depending on the intensity of incident light. PMT 1 outputs a contamination-detection signal current based on light scattered and reflected by a contaminant and the like. In the detection part 10, an I-V conversion module 2 including a resistor 4 and an operational amplifier 5 converts the contamination-detection signal current into a detection voltage signal. Further, in the detection circuit 3, a logarithmic amplifier 6 logarithmically amplifies the detection voltage signal making an input voltage 8 to the detection circuit 3 so that a minute voltage can be detected even with the minimum resolution of an analog-to-digital conversion circuit 7, and then the analog-to-digital conversion circuit 7 converts the amplified voltage to a digital value. Subsequently, the resultant digital signal having the digital value is output to a data processing circuit (not shown) as an output code 9, and then a judgment about a contaminant or the like is made.

In general, the intensity of light scattered from a contaminant with a minute particle size is said to be proportional to about the sixth power of the diameter of the contaminant. Therefore, in the case where a wafer targeted for inspection is irradiated with light, and scattered light produced by the irradiation is used to detect a contaminant, a detection circuit for detecting a contaminant is required to have a wider dynamic range, which depends on the range of the amplitudes of detected signals. This is because the smaller the contaminant on a wafer is, the minuter the detected signal is. Further, when the number of rotations of a wafer is increased in order to shorten the time for inspecting the wafer, scanning of a surface of the wafer is speeded up, which results in an increase in the rate of change of the detected signal per hour. Therefore, it is required to speed up the operation of the detection part.

Now, as for an analog-to-digital conversion circuit, there is a basic trade-off relation between its processing speed and dynamic range in general. Therefore, the dynamic range of the analog-to-digital conversion circuit tends to decrease with an increase in the speed, and its minimum resolution has a tendency to increase.

Hence, a method to widen the dynamic range by means of arranging amplifiers in parallel, which amplify a detection current with different amplification factors, and using, of outputs of the amplifiers, an output of an appropriate range as the technique disclosed by JP-A-8-145899 has been proposed in the art.

SUMMARY OF THE INVENTION

According to the technique as disclosed by JP-A-8-145899, an analog-to-digital conversion circuit is arranged for each of the ranges which the amplifiers are responsible for. Therefore, the dynamic range of the whole detection part can be widened even in the situation where the dynamic range of each analog-to-digital conversion circuit is restricted owing to the speedup.

However, the technique has a problem such that it is required to adjust the amplification factors of the amplifiers or to select their components thereby to fit the ratios of the amplification factors to design values because the amplifiers perform detections with different ranges, and therefore the difference in detection error at the time of switching between their detection ranges arises in nature, which lowers the accuracy of measurement.

The invention was made in consideration of the problems as described above, and it provides a method for detection and a semiconductor wafer contamination-inspecting apparatus using the method, which can speed up the operation of the detection circuit and widening of the dynamic range thereof, and which can achieve the higher accuracy by correcting the difference in detection error caused by switching between detection ranges.

A method for detection according to the invention and a semiconductor wafer contamination-inspecting apparatus using the method are characterized in: in a detection part are disposed amplification modules having different amplification factors and detection systems each having an analog-to-digital conversion circuit and a logarithmic conversion module; and an output code composed of an output of at least one of the detection systems is compared with switching data to switch between the output code and an output code composed of an output of the other detection system and selectively output the output codes.

The detection part according to the invention has the following features. That is, in the detection part are disposed a reference voltage output module for producing a reference voltage, and a switching means for switching between an input voltage to the detection part and the reference voltage to selectively apply the voltages to the detection systems. Also, in the detection part are disposed a means for applying the reference voltage to the detection systems, a means for computing a difference between output codes output by circuits of the detection systems, and a means for holding the resultant difference as a piece of correction data. Thus, when a numerical computation to derive the correction data is performed on an output code of one of the detection systems on input of voltage of a detected signal to the detection part, output codes output by the detection systems are coincident with each other in the condition where a detection voltage equivalent to the reference voltage is input to the detection part.

As for the detection method, the detection systems speed up the operation of the detection circuit and widen the dynamic range thereof. Further, the difference in detection error between ranges is corrected at the time of switching the outputs of the detection systems, whereby the higher accuracy of the detection part can be achieved.

Now, the outline of the preferred forms of the invention will be described below briefly.

(1) According to the first aspect of the invention is provided a contamination-inspecting apparatus for inspecting a wafer surface for a contaminant including: an irradiation optical system for irradiating the wafer surface with laser light; a detection optical system for detecting light scattered from the wafer surface; and a detection unit for converting the scattered light detected with the detection optical system into an electric signal to make a correction, wherein the contamination-inspecting apparatus, the detection unit has a plurality of detection circuits with different amplification factors, and the detection unit has a means for correcting the electric signal by use of a piece of correction data derived from a difference in amplification factor between the plurality of detection circuits and held in advance.

(2) According to the second aspect of the invention is provided the contamination-inspecting apparatus as stated in (1), wherein the detection unit has a switching means for switching between a piece of output data of a first detection circuit and a piece of data output by a second detection circuit and then corrected based on the piece of correction data thereby to selectively output the pieces of data, provided that the first and second detection circuits are each one of the plurality of detection circuits.

(3) According to the third aspect of the invention is provided the contamination-inspecting apparatus as sated in (2), wherein the first detection circuit has a first amplification means, and a first analog-to-digital conversion circuit for sampling an output of the first amplification means, the second detection circuit has a second amplification means, and a second analog-to-digital conversion circuit for sampling an output of the second amplification means, and the piece of correction data is calculated from a piece of output data of the first analog-to-digital conversion circuit and a piece of output data of the second analog-to-digital conversion circuit when a reference voltage is applied to the first and second amplification means.

(4) According to the fourth aspect of the invention is provided a detection circuit which detects a voltage and outputs a code corresponding to the voltage, including: a reference-voltage generation means for producing and outputting a reference voltage; a switching means for performing switching between an input to the detection circuit and an output of the reference-voltage generation means; a first amplification means for amplifying an output of the switching means; a first analog-to-digital conversion circuit for sampling an output of the first amplification means; a second amplification means for amplifying the output of the switching means; a second analog-to-digital conversion circuit for sampling an output of the second amplification means; a computing means for calculating a piece of correction data from a piece of output data of the first analog-to-digital conversion circuit and a piece of output data of the second analog-to-digital conversion circuit when the reference voltage is applied to the first and second amplification means with the switching means; a correction means for making a correction of a piece of output data of at least one of the first and second analog-to-digital conversion circuits by use of the piece of correction data calculated by the computing means; and a switching means for switching between the piece of output data of the analog-to-digital conversion circuit and a piece of data resulting from the correction of the piece of output data to selectively output the pieces of data.

These and other objects, features and advantages of the invention will be apparent from the following more particular description of preferred embodiments of the invention as illustrated in the accompanying drawings.

DESCRIPTION OF THE PREFERRED EMBODIMENTS

The embodiments of the invention will be described below in detail with reference to the drawings. In all the drawings, which are referred to in explaining the embodiments, like parts are identified by the same reference character, numeral or label in principle, and iteration of the description thereof is eliminated.

Of an irradiation optical system, a detection optical system, a detection unit and a display unit included in the contamination-inspecting apparatus, particularly the detection part of the detection unit will be described here taking an example. As to the others, it is needless to say that appropriate use of a publicly known art will suffice.

EXAMPLE 1

Figure 1:
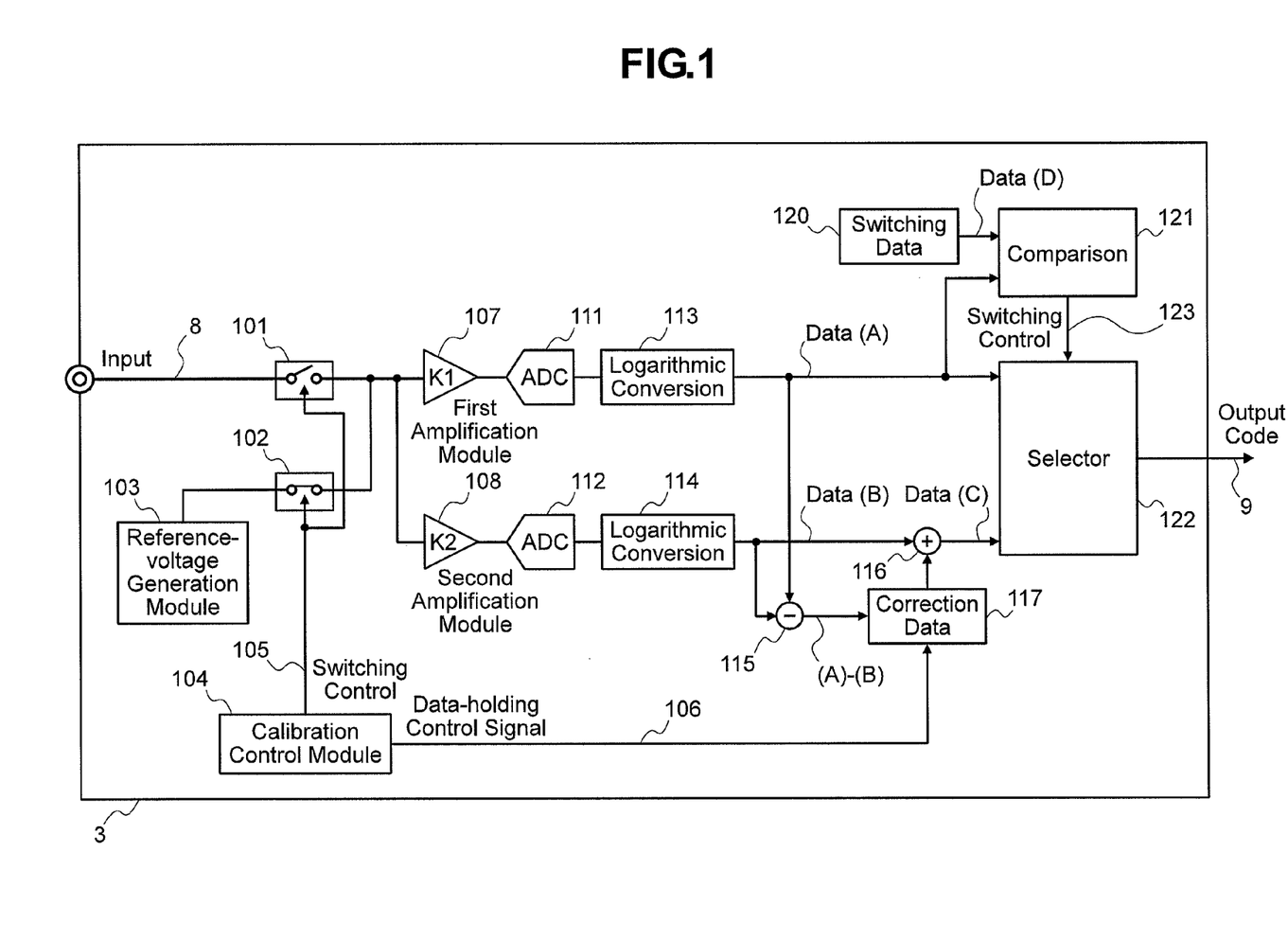
FIG. 1 is a diagram showing a configuration of a detection circuit according to the first embodiment of the invention.
Figure 5:
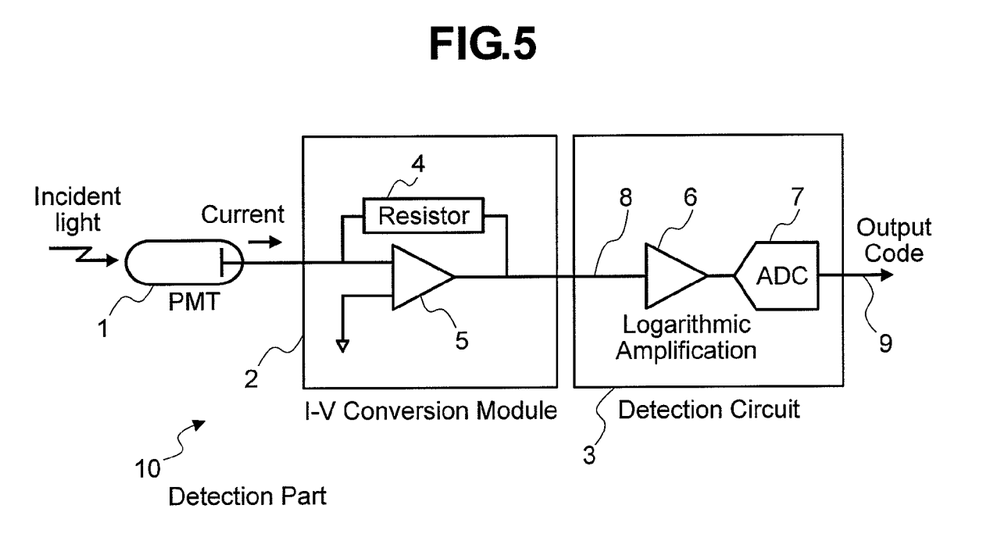
FIG. 5 is a diagram showing a configuration of a detection part of a conventional contamination-inspecting apparatus, considered as a related art.

A configuration of the detection part of the semiconductor wafer contamination-inspecting apparatus according to the first embodiment of the invention is shown in FIG. 1. The detection part is operable to output a digital value according to a predetermined operation as described below based on a detection voltage signal output by the I-V conversion module 2 of the semiconductor wafer contamination-inspecting apparatus as shown in FIG. 5, for instance. The detection part 3 includes: a switch 101 to which an input voltage 8 is applied; a reference-voltage generation module 103 for generating a reference voltage; a switch 102 to which a reference voltage generated by the reference-voltage generation module 103 is applied; a calibration control module 104 which performs switching control of the switches 101 and 102 by means of a switching control signal 105; amplification modules 107 and 108 to which a voltage is input through the switches 101 and 102; analog-to-digital conversion circuits 111 and 112 to which voltages amplified by the amplification modules 107 and 108 are input; logarithmic conversion modules 113 and 114 which perform logarithmic conversion of codes output by the analog-to-digital conversion circuits 111 and 112; a comparison module 121 which compares switching data held by a switching data-holding module 120 with the data (A) output by the logarithmic conversion module 113; a subtraction module 115 which executes, based on the data (A) and data (B) output by the logarithmic conversion module 114, a process of subtracting the data (B) from the data (A), expressed by (A)-(B); a data-holding module 117 which holds data output by the subtraction module 115 according to a holding-control signal 106 from the calibration control module 104; an addition module 116 which performs a process of adding the data held by the data-holding module 117 and the data (B) to output data (C); and a selector 122 which switches the data (A) and data (C) according to a switching-control signal 123 from the comparison module 121 to output either the data (A) or data (C) as a output code 9 output by the detection part.

Figure 2A:
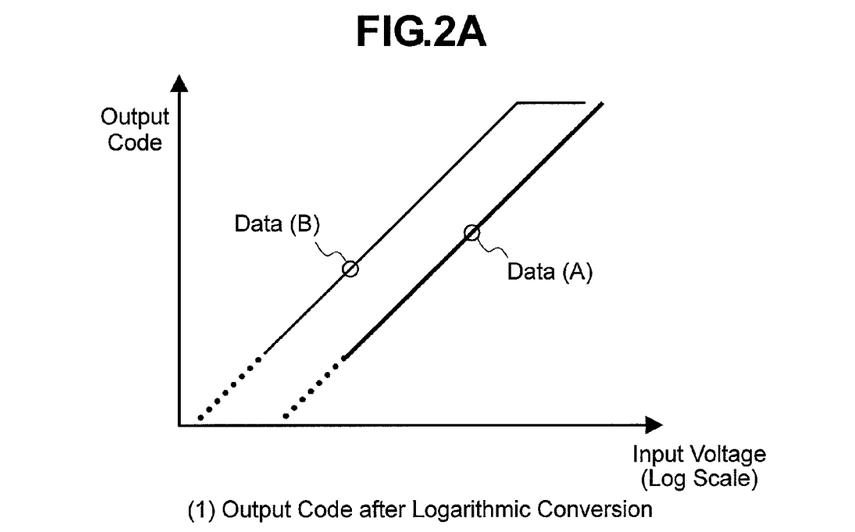
FIGS. 2A and 2B are each a diagram showing the relation between input voltages and output codes in association with the detection circuit according to the first embodiment.

The amplification modules 107 and 108 have amplification factors set to K1 and K2 respectively. Here, when the amplification factors are set so that K1<K2 (Expression 1) holds, the relation between the data (A) and data (B) output by the logarithmic conversion modules 113 and 114 after the processing by the analog-to-digital conversion circuits 111 and 112 becomes as shown in FIG. 2A, i.e. the data (B) are larger than the data (A) with respect to a common input voltage. In FIGS. 2A and 2B, the axes of input voltages are presented on the logarithmic scale. The conversion characteristic as shown in FIG. 2A has been obtained as a result of the conversion by the logarithmic conversion modules 113 and 114. Specifically, as to the characteristic curves of the data (A) and (B), the ratio of the amplification factors described above results in a fixed code difference as shown in FIG. 2A because of the logarithmic conversions by the logarithmic conversion modules 113 and 114. As in FIG. 2A, the data (B) increases with an increase of the input voltage, which shows the characteristic that when an output of the amplification module 108 or an input of the analog-to-digital conversion circuit 112 becomes saturated, the data (B) becomes saturated, and makes a fixed output code.

Before a detecting operation by the detection part 3, calibration is performed according to a control signal (not shown) from the outside. In the calibration, the calibration control module 104 performs the control using a switching control signal 105 so that the switches 101 and 102 are turned off and on respectively, and the reference voltage from the reference-voltage generation module 103 is applied to the amplification modules 107 and 108. In this situation, the code (A)-(B) output by the subtraction module 115 is held as correction data by the data-holding module 117 according to the data holding-control signal 106. Then, the data (B) is corrected with the correction data, whereby the data (C), which is an output from the addition module 116, is made equal to the data (A). In other words, the data (C) is made to agree with the data (A) in characteristic.

Figure 2B:
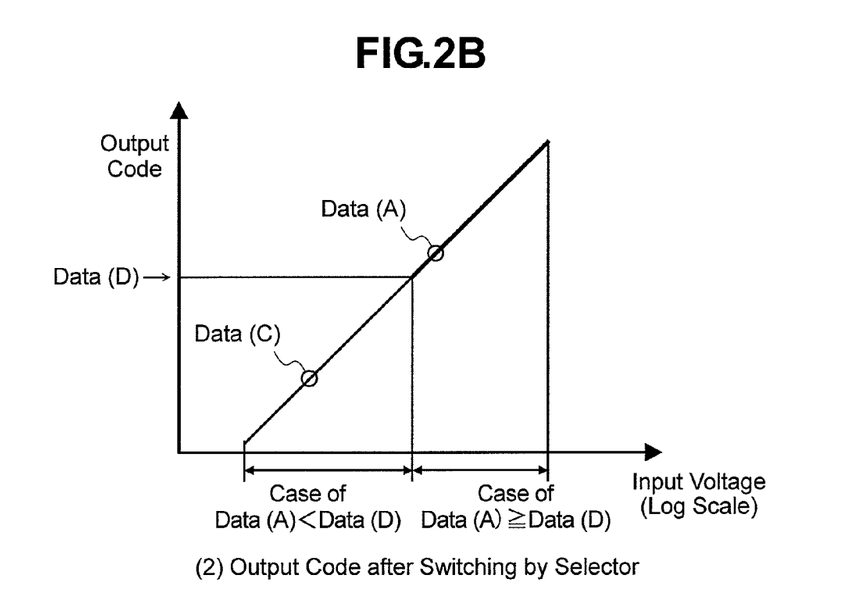

Subsequently, to execute the detecting operation by the detection part 3, a control signal (not shown) from the outside is used to bring the detection part 3 to a condition for the detecting operation. Specifically, the calibration control module 104 performs the control using the switching control signal 105 so that the switches 101 and 102 are turned on and off respectively, and the input voltage 8 to the detection circuit 8 is applied to the amplification modules 107 and 108. In the detection part 3, a comparison of the data (A) with data (D), which is switching data, is made constantly. When the data (A) is equal to or larger than the data (D), the data (A) is output as the output code 9 through the selector 122, whereas when the data (A) is smaller than the data (D), the data (C) is output as the output code 9. In this situation, the data (A) and data (C) are coincident with each other in characteristic as described above. The output code 9 of the detection part 3 with respect to an input voltage to the detection part 3 exhibits the conversion characteristic as shown in FIG. 2B.

As stated above, in performing the detection with different ranges using two or more amplifiers, the detection part according to the first embodiment corrects the ratios between amplification factors of the amplifiers based on correction data detected when a reference voltage is applied. Thus, the detection part can reduce the difference in detection error between the ranges at the time of switching the ranges, thereby to enhance the accuracy of a detection part with a higher accuracy.

In the above description, the principle of operation of the detection part according to the first embodiment has been described with reference to FIGS. 1 and 2 briefly. However, the detection part may be arranged so that the reference-voltage generation circuit 103 switches the reference voltage to appropriate levels, whereby correction data is detected at two or more points and e.g. CPU performs numerical computations based on the correction data. It is needless to say that the detection part can cope with this case by an arrangement such that the part constituted by the addition module 116 serves as a memory to store LUT (Look Up Table) and the like, into which the CPU writes data.

EXAMPLE 2

Next, a detection part of a semiconductor wafer contamination-inspecting apparatus according to the second embodiment of the invention will be described with reference to FIG. 3. The second embodiment is mainly characterized in that the detection part 3 includes a logarithmic amplification module 109 and a linear amplification module 110. Other parts of the detection part 3 are arranged in the same way as in the first embodiment.

In the first embodiment, when the amplitude of the input voltage 8 to the detection circuit is larger, and thus the output voltage of the amplification module 107 is beyond the input-allowable bounds of the analog-to-digital conversion circuit 111, the output code of the analog-to-digital conversion circuit 111 is saturated and therefore the input voltage 8 of the detection circuit cannot be detected accurately.

Figure 3:
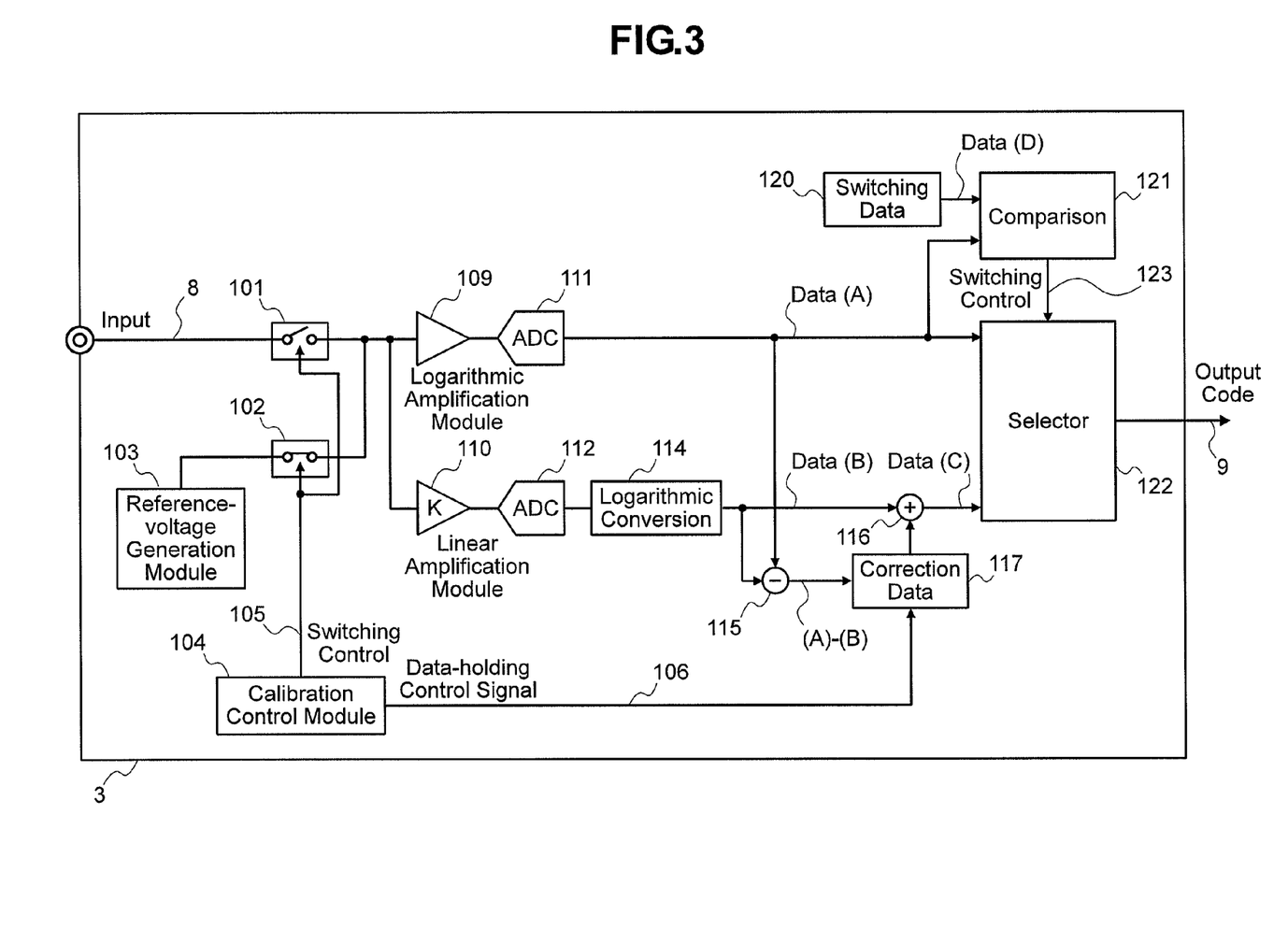
FIG. 3 is a diagram showing a configuration of a detection circuit according to the second embodiment of the invention.

For that reason, in the detection part according to the second embodiment, a logarithmic amplification module 109 is disposed on the input side of the analog-to-digital conversion circuit 111 as shown in FIG. 3, and logarithmic conversion of an input voltage 8 to the detection part is performed. As a result, even when the amplitude of the input voltage 8 to the detection part is larger, it becomes possible to prevent the saturation of the analog-to-digital conversion circuit 111.

In this case, the digital logarithmic conversion module 113 as described in the first embodiment is not placed in the stage subsequent to the analog-to-digital conversion circuit 111, and the data output by the analog-to-digital conversion circuit 111 are handled as detection data (A) directly. Further, the logarithmic conversion module 114 is arranged so as to have the same logarithmic conversion characteristic as that of the logarithmic amplification module 109. Thus, in regard to the relation between the input voltage 8 to the detection part and the output code 9 in the detection part 3, the characteristic as shown in FIG. 2B can be obtained.

To correct the variation in the conversion characteristic of the logarithmic conversion module 109, the detection part 3 may be arranged so that the following are performed: switching the output voltage of reference-voltage generation module 103 to an appropriate level; detecting and holding correction data at levels; and conducting numerical computations of the correction data using e.g. CPU; and correcting the detection data making use of the memory function such as the LUT.

EXAMPLE 3

Figure 4:
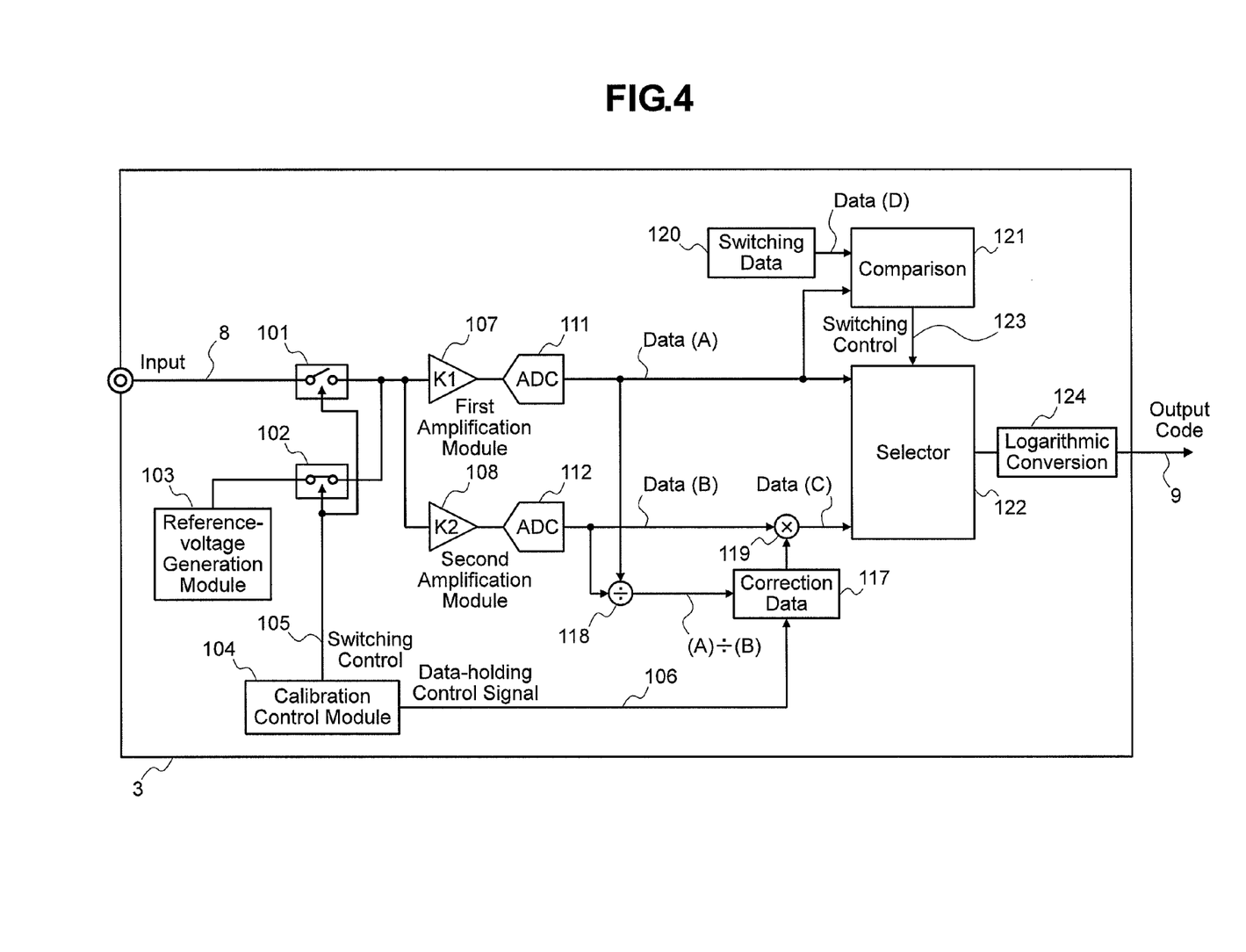
FIG. 4 is a diagram showing a configuration of a detection circuit according to the third embodiment of the invention.

Next, a detection part of a semiconductor wafer contamination-inspecting apparatus according to the third embodiment of the invention will be described with reference to FIG. 4. The third embodiment is mainly characterized in that the detection part 3 includes: a division module 118 which performs a computation of correction data, expressed by (A)÷(B) from the data (A) output by the analog-to-digital conversion circuit 111 and the data (B) output by the analog-to-digital conversion circuit 112; a multiplication module 119 which performs a multiplication of the correction data held in the data-holding module 117 and the data (B) thereby to output data (C); a logarithmic conversion module 124 which performs a logarithmic conversion of the data output by the selector 122 thereby to output an output code. Other parts of the detection part 3 are arranged in the same way as in the first embodiment.

According to the arrangement of the detection part in association with the third embodiment, the division module 118 calculates the ratio of the data (A) to the data (B), and the multiplication module 119 multiplies the ratio by the data (B). Then, the ratio of amplification factors of the amplification modules 107 and 108 is corrected, provided that the amplification factors have been set to be different from each other. This makes the data (A) and data (C) substantially equivalent to data detected with two amplifiers identical to each other in amplification factor. The resultant pieces of data are output through the logarithmic conversion module 124. Thus, as to the relation between the input voltage 8 to the detection part and the output code 9, the characteristic as shown in FIG. 2B is achieved.

While the invention made by the inventor has been described above focusing on the embodiments, the invention is not so limited. It is needless to say that various modifications and changes may be made without departing from the subject matter thereof. For instance, as to any of the above-described embodiments, the case where two detection circuits are included has been shown. However, the invention is not so limited, and three or more detection circuits may be incorporated.

Now, the effects and advantages achieved by the preferred embodiments of the invention disclosed herein will be described briefly.

The invention can widen the dynamic range of a semiconductor wafer contamination-inspecting apparatus with a higher accuracy.

Further, according to the invention, a contamination-inspecting apparatus is arranged so that in a detection circuit thereof, correction data is detected based on a reference voltage thereby to correct the difference in detection error caused by switching between detection ranges. Thus, the speedup of the operation of the detection circuit, widening of the dynamic range, and enhancement of the accuracy are achieved.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A contamination-inspecting apparatus for inspecting a wafer surface for a contaminant comprising:
    an irradiation optical system for irradiating the wafer surface with laser light;
    a detection optical system for detecting light scattered from the wafer surface; and
    a detection unit for converting the scattered light detected with the detection optical system into an electric signal to make a correction;
    wherein the detection unit has a plurality of detection circuits with different amplification factors; and
    wherein the detection unit has a means for correcting the electric signal by use of a piece of correction data derived from a difference in amplification factor between the plurality of detection circuits and held in advance; and
    wherein the detection unit has a switching means for switching between a piece of output data of a first detection circuit and a piece of data output by a second detection circuit and then corrected based on the piece of correction data thereby to selectively output the pieces of data, provided that the first and second detection circuits are each one of the plurality of detection circuits.

2. The contamination-inspecting apparatus according to claim 1, wherein the switching means performs the switching based on a result of comparison with a piece of preset switching data.

3. The contamination-inspecting apparatus according to claim 2, wherein the switching means compares the piece of preset switching data with the piece of output data of the first detection circuit, and performs the switching according to a relation between magnitudes of the pieces of data.

4. The contamination-inspecting apparatus according to claim 1, wherein the first detection circuit has a first amplification means, and a first analog-to-digital conversion circuit for sampling an output of the first amplification means,
    the second detection circuit has a second amplification means, and a second analog-to-digital conversion circuit for sampling an output of the second amplification means, and
    the piece of correction data is calculated from a piece of output data of the first analog-to-digital conversion circuit and a piece of output data of the second analog-to-digital conversion circuit when a reference voltage is applied to the first and second amplification means.

5. A detection circuit which detects a voltage and outputs a code corresponding to the voltage, comprising:
    a reference-voltage generation means for producing and outputting a reference voltage;
    a switching means for performing switching between an input to the detection circuit and an output of the reference-voltage generation means;
    a first amplification means for amplifying an output of the switching means;
    a first analog-to-digital conversion circuit for sampling an output of the first amplification means;
    a second amplification means for amplifying the output of the switching means;
    a second analog-to-digital conversion circuit for sampling an output of the second amplification means;
    a computing means for calculating a piece of correction data from a piece of output data of the first analog-to-digital conversion circuit and a piece of output data of the second analog-to-digital conversion circuit when the reference voltage is applied to the first and second amplification means with the switching means;

a correction means for making a correction of a piece of output data of at least one of the first and second analog-to-digital conversion circuits by use of the piece of correction data calculated by the computing means; and a switching means for switching between the piece of output data of the analog-to-digital conversion circuit and a piece of data resulting from the correction of the piece of output data to selectively output the pieces of data.

6. The detection circuit according to claim 5, wherein logarithmic conversion is performed on a piece of output data of at least one of the first and second analog-to-digital conversion circuits.

7. The detection circuit according to claim 5, further comprising a means for logarithmically amplifying an input signal.

8. The detection circuit according to claim 5, further comprising a comparison means for comparing one of a piece of output data of at least one of the first and second analog-to-digital conversion circuits and a piece of data resulting from the correction of the output data with an appropriate piece of data, wherein the switching means outputs one of the piece of output data of the analog-to-digital conversion circuit and a piece of data resulting from the correction of the output data, according to a result of the comparison by the comparison means.

9. A contamination-inspecting apparatus for inspecting a wafer surface for a contaminant, comprising:

an irradiation optical system for irradiating the wafer surface with laser light;

a detection optical system for detecting light scattered from the wafer surface; and a detection unit for converting the scattered light detected with the detection optical system into an electric signal to make a correction, wherein the detection unit has the detection circuit according to any one of the claims 5 to 8.

\* \* \* \* \*